United States Patent [19]

Wada et al.

[11] Patent Number: 4,966,966

[45] Date of Patent: Oct. 30, 1990

[54] PROCESS FOR PREPARING SUCROSE FATTY ACID ESTERS

[75] Inventors: Keisuke Wada, Yokohama; Kazuhiko Onuma, Machida; Takashi Ushikubo, Yokohama; Tsuyoshi Ito, Machida, all of Japan

[73] Assignee: Mitsubishi Chemical Industries Limited, Japan

[21] Appl. No.: 144,575

[22] Filed: Jan. 14, 1988

[30] Foreign Application Priority Data

Jan. 17, 1987 [JP] Japan .................................. 62-8718

[51] Int. Cl.$^5$ ..................... C07H 1/00; C07H 13/06
[52] U.S. Cl. ..................... 536/119; 536/1.1; 536/115; 536/124
[58] Field of Search ............. 536/1.1, 115, 119, 124

[56] References Cited

U.S. PATENT DOCUMENTS

| | | | |
|---|---|---|---|
| 2,931,802 | 4/1960 | Touey et al. | 536/119 |
| 3,096,324 | 7/1963 | Goins et al. | 536/119 |
| 3,103,507 | 9/1963 | Knoevenagel | 536/115 |
| 3,251,827 | 5/1966 | Schnell et al. | 436/119 |
| 4,032,702 | 6/1977 | James | 536/115 |
| 4,306,062 | 12/1981 | Jones | 536/115 |
| 4,322,523 | 3/1982 | Wagner | 536/120 |
| 4,377,685 | 3/1983 | Bouniot et al. | 536/119 |
| 4,377,686 | 3/1983 | Feuge et al. | 536/119 |
| 4,399,149 | 8/1983 | Haken et al. | 514/551 |
| 4,517,360 | 5/1985 | Volpenhein | 536/119 |
| 4,691,041 | 9/1987 | Duranleau et al. | 558/277 |

FOREIGN PATENT DOCUMENTS

| | | |
|---|---|---|
| 51-14486 | 5/1976 | Japan . |
| 53-6130 | 3/1978 | Japan . |
| 57-203095 | 12/1982 | Japan . |
| 61-189289 | 8/1986 | Japan . |
| 61-212593 | 9/1986 | Japan . |
| 0912595 | 12/1962 | United Kingdom . |
| 0925718 | 5/1963 | United Kingdom . |
| 1050452 | 12/1966 | United Kingdom . |
| 1322706 | 7/1973 | United Kingdom . |
| 2065634 | 7/1981 | United Kingdom . |

OTHER PUBLICATIONS

Feuge et al; J.A.O.C.S. 47(2):56–60 (1970).
Stavitskaya et al; Chemical Abstracts 96:141370q (1982).
Kurihara et al; Chemical Abstracts 108:23683n (1988).
Wolf; Ion Exch. Process Ind., Pap. Conf.; Soc. Chem. Ind. Meeting date 1969 Published 1970 pp. 285–290.
Setinek; Collection Czechoslov. Chem. Commun. 42: 979–986 (1977).
Bhagade et al; Chemical & Petro-Chemicals Journal 9(7): 3–12 (1978).

*Primary Examiner*—Ronald W. Griffin
*Assistant Examiner*—Nancy S. Carson
*Attorney, Agent, or Firm*—Jordan B. Bierman

[57] ABSTRACT

A process for preparing a sucrose fatty acid ester by interesterification between sucrose and a lower alkanol ester or glyceride of a fatty acid in the presence of an ion exchange resin is disclosed, wherein said ion exchange resin is a cation exchange resin having a carboxyl group having been ion-exchanged with an alkali metal and/or an alkaline earth metal. A sucrose fatty acid can be prepared in a high yield through a simplified recovery and purification step.

4 Claims, No Drawings

PROCESS FOR PREPARING SUCROSE FATTY ACID ESTERS

FIELD OF THE INVENTION

This invention relates to a process for preparing a sucrose fatty acid ester. More particularly, it relates to a process for preparing a sucrose fatty acid ester by interesterification between sucrose and a lower alkanol ester or glyceride of a fatty acid in the presence of an ion exchange resin as a catalyst.

BACKGROUND OF THE INVENTION

Sucrose fatty acid esters exhibit excellent surface activity, satisfactory biological decomposability and high stability and have, therefore, been widely employed as additives for foods, cosmetics, pharmaceuticals, kitchen detergents, feeding stuff, resins, etc. or as assistants in the field of the chemical industry, for example, for polymerization reaction, oxidation reaction, and the like.

Extensive studies have hitherto been conducted on processes for preparing the sucrose fatty acid esters having such a wide variety of uses. Main processes so far developed comprise interesterification between sucrose and a lower alkanol ester or glyceride of a fatty acid (hereinafter referred to as a fatty acid ester) and are classified into the following three large groups.

Processes of the first group are included under a solvent process which comprises reacting sucrose and a fatty acid ester in a homogeneous system using a solvent capable of dissolving both the reactants, such as dimethylformamide, dimethyl sulfoxide, etc. According to this process, the reaction usually proceeds at low temperatures of about 90° C. under reduced pressure. Catalysts which can be used include oxides, hydroxides, carbonates or hydrogencarbonates of alkali metals or alkaline earth metals, etc., with potassium carbonate being particularly preferred.

Processes of the second group comprise dissolving sucrose in a solvent, such as propylene glycol, water, etc., dispersing the resulting solution and a fatty acid ester with the aid of an emulsifier (e.g., fatty acid soaps) to form a very fine dispersion, i.e., a microemulsion, and removing the solvent to effect the interesterification reaction (microemulsion process). This reaction is usually carried out at a temperature between 110° C. and 170° C. under reduced pressure.

Processes of the third group comprise directly reacting sucrose and a fatty acid ester without using solvent (direct process). The reaction is usually carried out at a temperature of from 110° C. to 140° C. under normal pressure.

However, any of these conventional processes have their own disadvantages as set forth below and still leave room for further improvements.

The third process, i.e., direct process, enjoys advantages in that no solvent is required and that the reaction proceeds under normal pressure, but the problem here is how to mix the sucrose and the fatty acid ester which are incompatible with each other. The problem has been solved by adding a fatty acid soap to the reaction system or forming a fatty acid soap in situ. However, existence of a fatty acid soap in the reaction system means that an additional procedure for separating and removing the fatty acid soap would be necessary for recovery and purification of the desired product just as required in the microemulsion process.

The microemulsion process and the direct process employ reaction temperatures between 110° C. and 170° C., that are higher than those required in the solvent process (about 90° C.), which results in considerable coloring of final products. In some extreme cases, the products should be subjected to a complicated decoloring treatment.

Considering hydropholic and lipophilic properties, that are significant characteristics of sucrose fatty acid esters, it is difficult to obtain sucrose fatty acid esters having a broad range of HLB value, a measure for hydrophilic and lipophilic properties commonly adopted in the art, by the microemulsion process or the direct process.

On the other hand, according to the solvent process, the products obtained are less colored as compared with those of the other processes owing to the relatively low reaction temperatures and may have a broadened range of HLB value. However, since the both reactants and the catalyst form a uniform solution in the presence of a solvent, it is necessary to add an acid to the reaction system for neutralization in order to stop the reaction so as to achieve desired reaction rate and degree of ester replacement. More specifically, in the case of using, for example, potassium carbonate as a catalyst, the reaction should be stopped by adding lactic acid, phosphoric acid or a solution containing the same, etc. to the reaction solution taking care on pH of the reaction solution Without this neutralization step, the reaction would further proceed due to the presence of the catalyst having interesterification activity even in the recovery and purification step of the product, which leads to reduction of yield of sucrose fatty acid esters having desired structure and composition. The neutralization step, in turn, brings about different problems, that is, water produced by the neutralization should be removed by a dehydration step, and the recovery and purification step becomes complicated because the reaction mixture contains a neutralization product, e.g., potassium lactate in the case of neutralizing a potassium carbonate catalyst with lactic acid or a lactic acid solution. Further, when the unreacted material, e.g., sucrose, is recylized to the reaction system, if potassium lactate is present in the recylized sucrose, the solubility of the potassium carbonate catalyst in the reaction solution is reduced to decrease the reaction rate.

SUMMARY OF THE INVENTION

One object of this invention is to provide an improved process for preparing a sucrose fatty acid ester.

Another object of this invention is to provide a process for preparing a sucrose fatty acid ester, in which the produced sucrose fatty acid ester and a catalyst used can easily be separated and recovered.

A further object of this invention is to provide a process for preparing a sucrose fatty acid ester, in which the produced sucrose fatty acid ester can be recovered and purified through simplified steps.

The present invention relates to a process for preparing a sucrose fatty acid ester comprising interesterification between sucrose and a lower alkanol ester or glyceride of a fatty acid in the presence of an ion exchange resin, wherein said ion exchange resin is a cation exchange resin having a carboxyl group having been ion-exchanged with an alkali metal and/or an alkaline earth metal as a functional group.

DETAILED DESCRIPTION OF THE INVENTION

The lower alkanol ester of a fatty acid which can be used in the present invention includes esters formed by saturated or unsaturated fatty acids having from 6 to 24 carbon atoms and saturated or unsaturated alcohols having from 1 to 4 carbon atoms, such as methyl caprate, methyl laurate, methyl palmitate, methyl stearate, methyl oleate, methyl behenate, butyl stearate, etc. These fatty acid esters may be used either individually or in combinations thereof.

While the present invention is concerned with the preparation of sucrose fatty acid esters by interesterification between sucrose as a polyhydric alcohol and a fatty acid ester, it is also applicable with advantage to reactions of other polyhydric alcohols than sucrose, for example, glycerin, polyglycerin, and sugars, e.g., glucose, fructose, maltose, lactose, etc.

The interesterfication reaction of sucrose and the fatty acid ester may be effected either in the absence or in the presence of a solvent. Taking small compatibility between these reactants into consideration, it is preferable to use a solvent capable of dissolving both of them. Specific examples of such a solvent include dimethyl sulfoxide, dimethylformamide, pyridine, N-methylpyrrolidone, etc. The mode and conditions of the reaction vary depending on the reaction vessel used, the kind of the lower alkanol ester or glyceride of a fatty acid, the solvent and the catalyst, and the like. In general, the reaction is carried out at a temperature of from about 40° to 100° C. under a pressure of from normal pressure to several mmHg. Reaction temperatures exceeding 100° C. cause serious coloring of the resulting sucrose fatty acid ester.

Since the interesterification reaction of the present invention is an equilibrium reaction, the alcohol by-produced by the reaction is preferably removed out of the reaction system to increase the yield of the desired product.

The cation exchange resin which can be used in the present invention has a carboxyl group having been ion-exchanged with an alkali metal and/or alkaline earth metal but still shows basicity. The cation exchange resin to be used may have various chemical and physical structures. With respect to physical structure, the resin may have either a gel structure or a porous structure and may have a wide range of degree of crosslinking.

Typical examples of preferred ion exchange resins to be used in the present invention are described below for illustrative purposes only but not for limitation.

(i) Cation exchange resins composed of a crosslinked high polymer of acrylic acid, methacrylic acid, etc., as a matrix and having a carboxyl group as a functional group.

Specific examples of this type are "Diaion WK" produced by Mitsubishi Chemical Ind., Ltd., "Amberlite IRC-50 and IRC-75" produced by Rohm & Haas Co., "Lewatit CNP 80" produced by Bayer A.G., "Dowex CCR-2" produced by Dow Chemical Co., etc.

(ii) Cation exchange resins having an iminodiacetate group of formula:

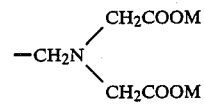

wherein represents an alkali metal ion and/or alkaline earth metal ion.

Specific examples of this type are "Diaion® CR-10" produced by Mitsubishi Chemical Ind., Ltd., "Amberlite® IR 718" produced by Rohm & Haas Co., "Lewatit® TP 207" produced by Bayer A.G., "Uniselex® UR 10 and UR 20" produced by Unitika Ltd., etc.

Since commercially available ion exchange resins are of, in general, H type, they should be ion-exchanged with an alkali metal and/or alkaline earth metal for use in the present invention. Ion exchanging can be carried out in a usual manner. The alkali metal and alkaline earth metal to be used here are not particularly limited and preferably include sodium, potassium, rubidium, and cesium. Some commercially available cation exchange resins have their carboxyl group ion-exchanged with an alkali metal and/or alkaline earth metal and can be, therefore, utilized as such in the present invention.

These ion exchange resins may be used either individually or in combinations of two or more thereof. It is effective for improving catalytic activity and selectivity to sucrose fatty acid esters that the ion exchange resin to be used is subjected to dehydration before contact with the reactants and the solvent.

The manner of contact of the reactants with the ion exchange resin includes a fixed bed, a suspending phase, a mobile bed, and the like. Further, the reaction may be carried out either in a batch system or in a continuous system.

The reaction conditions vary depending on the reaction mode, a desired HLB value of the resulting sucrose fatty acid ester, the kind of the lower alkanol ester of a fatty acid, the solvent, and the ion exchange resin to be used, and the like. Generally speaking, the temperature ranges from about 40° to 100° C.; the pressure ranges from normal pressure to several mmHg; the feeding ratio of sucrose to lower alkanol ester of a fatty acid ranges from about 0.1 to 10 by mole; the sucrose concentration ranges from about 1 to 80% by weight; and the concentration of the lower alkanol fatty acid ester ranges from about 1 to 60% by weight. In the case of performing the reaction in a suspending phase, for instance, the weight ratio of the ion exchange resin to the reaction mixture ranges from about 0.005 to 1, and the reaction period ranges from about 10 minutes to 30 hours.

According to the present invention, sucrose fatty acid esters of many uses as additives for foods, pharmaceuticals, etc. or as assistants in polymerization reaction and the like in the chemical industry can be obtained in high yields. Further, the product and the catalyst used can easily be separated and recovered thereby making the step for recovery and purification of the desired sucrose fatty acid ester simpler.

The cation exchange resin according to the present invention, with its carboxyl group as a functional group being ion-exchanged with an alkali metal and/or an alkaline earth metal, still shows basicity. Although anion exchange resins all show basicity, a basic anion exchange resin having a quaternary ammonium group as a functional group or a basic anion exchange resin having a tertiary amine as a functional group, when applied to the interesterification reaction to synthesize sucrose fatty acid esters, could not achieve satisfactory results.

The reason for the unsatisfactory activity or catalytic life of these basic anion exchange resins is not clear, but it would be assumed that the fine pores of the resin are clogged due to irreversible adsorption of certain organic substances, such as the reactants, the solvent, and the like, resulting in hinderance to reaction progress. It is well known in the art that regeneration of the resin having suffered such clogging is very difficult.

The present invention is now illustrated in greater detail with reference to Examples and Comparative Examples, but it should be understood that the present invention is not deemed to be limited thereto.

EXAMPLE 1

Preparation of Cation Exchange Resin Having Cs Type Carboxyl Group

In a 200 ml flask equipped with a stirrer were charged 100 ml of a 2N cesium hydroxide aqueous solution and 33.4 g of a methacrylic type porous weakly acidic cation exchange resin having a carboxyl group ("Diaion WK10", H type cation exchange resin produced by Mitsubishi Chemical Ind., Ltd.), and the mixture was stirred at room temperature for 3 hours to effect ion exchanging. The reaction mixture was filtered, washed with water, filtered, washed with methanol, filtered, and dried in a vacuum drier at 90° C. for 10 hours to prepare a cation exchange resin having a Cs type carboxyl group according to the present invention. The resulting cation exchange resin was designated as WK-10(Cs).

In a 500 ml flask equipped with a stirrer and a thermometer were charged 34.3 g (100 mmol) of sucrose, 15.0 g (50 mmol) of methyl stearate, and 125 g of dimethyl sulfoxide as a solvent. The mixture was heated up to 90° C. under stirring while evacuating the flask to a pressure of 25 mmHg. WK-10(Cs) as above prepared was added to the reaction system, followed by stirring at 90° C. and 25 mmHg for 6 hours to effect reaction.

After 1, 3, and 6 hours from the addition of WK-10(Cs), methanol contained in a trap placed in an evacuation line was quantitatively determined by gas chromatography. The results obtained are shown in Table 1.

As is obvious from a reaction formula, interesterification between sucrose and methyl stearate for synthesizing sucrose stearate is attended by production of one molecule of methanol per molecule of methyl stearate. Therefore, a methanol yield corresponds to a reaction rate of methyl stearate.

When the stirring was stopped after 6 hours' reacting, WK-10(Cs) readily precipitated apart from the reaction mixture. The separated reaction mixture was a light yellow uniform solution. The unreacted sucrose was determined by converting it to a TMS derivative by using 1,1,1,3,3,3-hexamethyldisilazane and trimethylchlorosilane and determining it by gas chromatography. The unreacted methyl stearate was directly determined by gas chromatography. The produced sucrose stearate was determined by high performance liquid chromatography. The results obtained are shown in Table 2 below.

The produced sucrose stearate was a mixture of a monoester, a diester, and a triester, with trace amounts of tetra- or higher order esters. The methanol content in the reaction mixture was negligibly small.

TABLE 1

| Reaction Time (hr) | Amount of Methanol Produced (mmol) | Yield of Methanol* (mol %) |
| --- | --- | --- |
| 1 | 25.7 | 51.4 |
| 3 | 49.0 | 97.9 |
| 6 | 50.0 | 100 |

Note:
*Based on the charged methyl stearate.

TABLE 2

| Composition of Reaction Solution | | | | | Reaction Rate of Sucrose (%) | Reaction Rate of Methyl Stearate (%) |
| --- | --- | --- | --- | --- | --- | --- |
| Sucrose (mmol) | Methyl Stearate (mmol) | Sucrose Stearate | | | | |
| | | Mono-ester (mmol) | Di-ester (mmol) | Tri-ester (mmol) | | |
| 59.2 | 0 | 23.1 | 11.9 | 3.9 | 40.8 | 100 |

EXAMPLES 2 TO 4

Ion exchanging was carried out in the same manner as in Example 1, except for replacing the 2N cesium hydroxide aqueous solution with a 2N aqueous solution of sodium hydroxide, potassium hydroxide or rubidium hydroxide to obtain a cation exchange resin having been ion-exchanged with Na, K, or Rb, respectively. The resulting cation exchange resin was designated as WK-10(Na), WK-10(K), or WK-10(Rb), respectively.

Interesterification was carried out in the same manner as in Example 1, except for using each of the resulting cation exchange resins to synthesize sucrose stearate. The results obtained are shown in Table 3. The reaction solution was light yellow in each case.

TABLE 3

| Example No. | Catalyst | Reaction Time (hr) | Composition of Reaction Solution | | | | | | Methanol Yield (mol %) | Reaction Rate of Sucrose (%) | Reaction Rate of Methyl Stearate (%) |
| --- | --- | --- | --- | --- | --- | --- | --- | --- | --- | --- | --- |
| | | | Methanol (mmol) | Sucrose (mmol) | Methyl Stearate (mmol) | Sucrose Stearate | | | | | |
| | | | | | | Mono-ester (mmol) | Di-ester (mmol) | Tri-ester (mmol) | | | |
| 2 | WK-10(Na) | 6 | 37.8 | 46.4 | 0.5 | 21.9 | 9.0 | 3.2 | 75.6 | 53.7 | 99.0 |
| 3 | WK-10(K) | 6 | 48.8 | 37.6 | 0.5 | 13.8 | 8.4 | 6.3 | 97.5 | 62.5 | 99.0 |
| 4 | WK-10(Rb) | 6 | 49.0 | 54.9 | 0 | 12.3 | 8.0 | 5.7 | 98.0 | 45.2 | 100 |

EXAMPLES 5 TO 7

Each of Amberlite IRC-50 (ion exchange resin produced by Rohm & Haas) and Diaion WK-11 and 13 (ion exchange resins produced by Mitsubishi Chemical Ind., Ltd.) which were structurally similar to but different in degree of crosslinking and the like from the ion exchange resin as used in Examples 1 to 4 was subjected to ion exchanging with a 2N KOH aqueous solution in the same manner as in Example 3 to obtain RC-50(K), WK-11(K), or WK-13(K), respectively.

Interesterification was carried out in the same manner as in Example 1, except for using each of the resulting cation exchange resins to synthesize sucrose stearate. The results obtained are shown in Table 4. The reaction solution was light yellow in each case.

TABLE 4

| Example No. | Catalyst | Reaction Time (hr) | Composition of Reaction Solution | | | | | | | Methanol Yield (mol %) | Reaction Rate of Sucrose (%) | Reaction Rate of Methyl Stearate (%) |
|---|---|---|---|---|---|---|---|---|---|---|---|---|
| | | | Methanol (mmol) | Sucrose (mmol) | Methyl Stearate (mmol) | Sucrose Stearate | | | | | |
| | | | | | | Mono-ester (mmol) | Di-ester (mmol) | Tri-ester (mmol) | | | | |
| 5 | IRC-50(K) | 6 | 45.0 | 55.3 | 2.9 | 23.9 | 8.1 | 2.4 | 89.9 | 44.8 | 94.3 |
| 6 | WK-11(K) | 6 | 42.8 | 50.5 | 2.1 | 24.9 | 8.2 | 2.2 | 85.6 | 49.6 | 95.9 |
| 7 | WK-13(K) | 6 | 44.7 | 46.9 | 4.0 | 24.2 | 7.6 | 2.1 | 89.3 | 53.0 | 92.0 |

EXAMPLES 8 TO 10

Sucrose stearate was synthesized in the same manner as in Example 1, except for using WK-10(Cs) as prepared in Example 1 as a catalyst and changing the composition of the starting materials as shown in Table 5 below. The results obtained are shown in Table 6. The reaction solution was light yellow in each case.

TABLE 5

| Example No. | Sucrose (mmol) | Methyl Stearate (mmol) | Dimethyl Sulfoxide (g) |
|---|---|---|---|
| 8 | 25 (8.6)* | 50 (15.0)* | 150.7 |
| 9 | 50 (17.1)* | 50 (15.0)* | 142.2 |
| 10 | 200 (68.5)* | 50 (15.0)* | 90.8 |

Note:
*Values in the parentheses are by weight (g).

TABLE 6

| Example No. | Reaction Time (hr) | Composition of Reaction Solution | | | | | | Methanol Yield (mol %) | Reaction Rate of Sucrose (%) | Reaction Rate of Methyl Stearate (%) |
|---|---|---|---|---|---|---|---|---|---|---|
| | | Methanol (mmol) | Sucrose (mmol) | Methyl Stearate (mmol) | Sucrose Stearate | | | | | |
| | | | | | Mono-ester (mmol) | Di-ester (mmol) | Tri-ester (mmol) | | | |
| 8 | 6 | 44.4 | 3.7 | 3.4 | 8.8 | 8.8 | 6.1 | 88.3 | 85.1 | 93.2 |
| 9 | 6 | 50.0 | 28.4 | 1.6 | 19.5 | 9.5 | 3.3 | 100 | 43.1 | 96.8 |
| 10 | 6 | 37.3 | 100.3 | 1.7 | 16.6 | 8.0 | 3.0 | 74.1 | 49.9 | 96.6 |

EXAMPLE 11 TO 13

A sucrose fatty acid ester was synthesized in the same manner as in Example 1, except for using WK-10(Cs) as prepared in Example 1 and replacing methyl stearate with methyl laurate, methyl palmitate or methyl oleate as shown in Table 7. The results obtained are shown in Table 8. The reaction solution was light yellow in each case.

TABLE 7

| Example No. | Kind of Fatty Methyl Ester | Sucrose (mmol) | Fatty Acid Methyl Ester (mmol) | Dimethyl Sulfoxide (g) |
|---|---|---|---|---|
| 11 | methyl laurate | 100 (34.3)* | 50 (10.8)* | 125 |
| 12 | methyl palmitate | 100 (34.3) | 50 (13.7) | 125 |
| 13 | methyl oleate | 100 (34.3) | 50 (14.8) | 125 |

Note:
*Values in the parentheses are by weight (g).

TABLE 8

| Example No. | Reaction Time (hr) | Composition of Reaction Solution | | | | | | | Methanol Yield (mol %) | Reaction Rate of Sucrose (%) | Reaction Rate of Methyl Stearate (%) |
|---|---|---|---|---|---|---|---|---|---|---|---|
| | | Methanol (mmol) | Sucrose (mmol) | Fatty Acid Ester (mmol) | Sucrose Ester | | | | | |
| | | | | | Mono-ester (mmol) | Di-ester (mmol) | Tri-ester (mmol) | | | | |
| 11 | 6 | 50 | 61.4 | 0 | 31.3 | 8.4 | 0.7 | 100 | 38.8 | 100 |
| 12 | 6 | 45.3 | 62.7 | 0.8 | 30.0 | 7.7 | 1.4 | 90.5 | 37.4 | 98.5 |
| 13 | 6 | 46.5 | 62.0 | 0.4 | 31.5 | 7.5 | 1.1 | 93.0 | 38.1 | 99.2 |

EXAMPLE 14

Sucrose stearate was synthesize in the same manner as in Example 1, except for using WK-10(Cs) as prepared in Example 1 as a catalyst, replacing dimethyl sulfoxide as a solvent with 125 g of N,N-dimethylformamide, and changing the reaction pressure to 95 mmHg. The results obtained are shown in Table 9 below. The reaction solution was light yellow in each case.

EXAMPLES 15 AND 16

Sucrose stearate was synthesized in the same manner as in Example 1, except for using WK 10(Cs) as prepared in Example 1 or WK-10(K) as prepared in Example 3 and performing the reaction under normal pressure. In these reaction systems, since methanol by-produced was present in the reaction mixture. The methanol as contained therein was quantitatively determined. The results obtained are shown in Table 10. The reaction solution was light yellow in each case.

TABLE 9

| Reaction Time (hr) | Composition of Reaction Solution | | | | | | Methanol Yield (mol %) | Reaction Rate of Sucrose (%) | Reaction Rate of Methyl Stearate (%) |
|---|---|---|---|---|---|---|---|---|---|
| | Methanol (mmol) | Sucrose (mmol) | Methyl Stearate (mmol) | Sucrose Stearate | | | | | |
| | | | | Mono-ester (mmol) | Di-ester (mmol) | Tri-ester (mmol) | | | |
| 6 | 39.4 | 61.1 | 10.7 | 27.0 | 5.3 | 0.6 | 78.8 | 39.0 | 78.8 |

TABLE 10

| Example No. | Catyalyst | Reaction Time (hr) | Composition of Reaction Solution | | | | | | Methanol Yield (mol %) | Reaction Rate of Sucrose (%) | Reaction Rate of Methyl Stearate (%) |
|---|---|---|---|---|---|---|---|---|---|---|---|
| | | | Methanol (mmol) | Sucrose (mmol) | Methyl Stearate (mmol) | Sucrose Stearate | | | | | |
| | | | | | | Mono-ester (mmol) | Di-ester (mmol) | Tri-ester (mmol) | | | |
| 15 | WK-10(Cs) | 6 | 26.2 | 43.2 | 23.8 | 18.2 | 3.3 | 0.5 | 52.4 | 56.8 | 52.4 |
| 16 | WK-10(K) | 6 | 22.1 | 61.4 | 27.9 | 15.9 | 2.4 | 0.5 | 44.2 | 38.6 | 44.2 |

COMPARATIVE EXAMPLE 1

In a 200 ml flask equipped with a stirrer were charged 100 ml of a 2N sodium hydroxide aqueous solution and 30.0 g of a styrene type high-porous strongly basic anion exchange resin ("Diaion HPA 25", Cl type anion exchange resin produced by Mitsubishi Chemical Ind., Ltd.), and the mixture was stirred at room temperature for 3 hours to effect ion exchanging. The reaction mixture was filtered, and the resin was washed with water followed by filtration, washed with methanol followed by filtration, and dried in vacuum drier at 90° C. for 10 hours.

When interesterification was carried out for 6 hours in the same manner as in Example 1, except for using the thus prepared ion exchange resin as a catalyst, neither sucrose stearate nor methanol was produced, and the resin turned to black.

COMPARATIVE EXAMPLE 2

Interesterification was carried out for a total reaction period of 15 hours in the same manner as in Example 1, except for using 55.6 g of a styrene type high-porous basic anion exchange resin ("Diaion WA-30", OH type anion exchange resin produced by Mitsubishi Chemical Ind., Ltd.). The results obtained are shown in Table 11. The reaction solution was light yellow.

aqueous solution, the activity to synthesize a sucrose fatty acid ester was not restrored.

COMPARATIVE EXAMPLE 3

Interesterification was carried out for 6 hours in the same manner as in Example 1, except for using 18.6 g of a styrene type weakly basic anion exchange resin ("Diaion WA-20", OH type anion exchange resin produced by Mitsubishi Chemical Ind., Ltd ). The amounts of sucrose stearate and methanol produced were both not more than 0.1 mmol.

COMPARATIVE EXAMPLE 4

Interesterification was carried out for 6 hours in the same manner as in Example 1, except for using 30.0 g of a styrene type strongly acidic cation exchange resin ("Amberlite 200®", Na type cation exchange resin produced by Rohm & Haas Co.) as a catalyst. The amounts of sucrose stearate and methanol produced were both not more than 0.1 mmol.

COMPARATIVE EXAMPLE 5

Interesterification was carried out for 6 hours in the same manner as in Example 1, except for using a resin prepared by stirring 30.0 g of the Na type cation exchange resin as used in Comparative Example 4 in a 2N hydrogen chloride aqueous solution for 3 hours to effect ion exchanging to an H type, followed by washing and drying. As a result, the amounts of sucrose stearate and methanol produced were both not more than 0.1 mmol. The resulting reaction mixture assumed black color and particularly showed considerable decomposition of sucrose.

TABLE 11

| Reaction Time (hr) | Composition of Reaction Solution | | | | | | Methanol Yield (mol %) | Reaction Rate of Sucrose (%) | Reaction Rate of Methyl Stearate (%) |
|---|---|---|---|---|---|---|---|---|---|
| | Methanol (mmol) | Sucrose (mmol) | Methyl Stearate (mmol) | Sucrose Stearate | | | | | |
| | | | | Mono-ester (mmol) | Di-ester (mmol) | Tri-ester (mmol) | | | |
| 1 | 11.8 | — | — | — | — | — | 23.6 | — | — |
| 3 | 30.7 | — | — | — | — | — | 61.4 | — | — |
| 6 | 31.2 | 64.5 | 17.0 | 18.0 | 5.0 | 1.7 | 62.3 | 35.5 | 66.0 |
| 8 | 31.3 | — | — | — | — | — | 62.5 | — | — |
| 12 | 31.5 | — | — | — | — | — | 62.9 | — | — |
| 15 | 31.5 | 64.5 | 17.0 | 17.9 | 4.9 | 1.7 | 63.0 | 35.5 | 66.0 |

It can be seen from Table 11 that the reaction for synthesizing a sucrose fatty acid ester came to a stop in about 3 hours from the commencement of the reaction. In an attempt of regeneration of the resin used in the reaction, the resin was washed with methanol, dimethyl sulfoxide, water, or the like followed by drying in a vacuum drier at 90° C. for 10 hours; or the thus treated resin was further treated with a 2N sodium hydroxide

COMPARATIVE EXAMPLES 6 TO 10

Interesterification was carried out for 6 hours in the same manner as in Example 1, except for using 10 g each of the basic inorganic solid acid catalysts shown in Table 12. In each case, the amounts of sucrose stearate and methanol produced were both not more than 0.1 mmol. The reaction mixtures obtained in Comparative Examples 9 and 10 assumed black color and particularly showed considerable decomposition of sucrose.

TABLE 12

| Comparative Example No. | Catalyst |
| --- | --- |
| 6 | $MgO^1$ |
| 7 | $CaO^2$ |
| 8 | $ZnO^3$ |
| 9 | $TiO_2^4$ |
| 10 | hydrated niobium oxide[5] |

Note:
[1]Product of Kishida Kagaku Co., Ltd.; heat treated under aeration at 400° C. for 5 hours
[2]Product of Kishida Kagaku Co., Ltd.; heat treated under aeration at 400° C. for 3 hours
[3]Product of Junsei Kagaku Co., Ltd.; heat treated under aeration at 400° C. for 3 hours
[4]Anatase type, heat treated under aeration at 400° C. for 3 hours
[5]Product of CBMM Co.; heat treated under aeration at 300° C. for 3 hours While the invention has been described in detail and with reference to specific embodiments thereof, it will be apparent to one skilled in the art that various changes and modifications can be made therein without departing from the spirit and scope thereof.

What is claimed is:

1. A process for preparing a sucrose fatty acid ester by interesterification between sucrose and a lower alkanol ester or glyceride of a fatty acid in the presence of an ion exchange resin, wherein said ion exchange resin is a cation exchange resin having a carboxyl group having been ion-exchanged with at least one of an alkali metal and an alkaline earth metal.

2. A process as claimed in claim 1, wherein said cation exchange resin comprises a high polymer obtained by crosslinking methacrylic acid as a matrix.

3. A process as claimed in claim 1, wherein said interesterification is carried out in the presence of a solvent.

4. A process as claimed in claim 3, wherein said solvent is dimethyl sulfoxide, dimethylformamide, pyridine, or N-methylpyrrolidone.

* * * * *